(12) United States Patent
Bloebaum (10) Patent No.: US 6,355,067 B1
(45) Date of Patent: *Mar. 12, 2002

(54) CEMENTED PROSTHETIC COMPONENT AND PLACEMENT METHOD

(75) Inventor: Roy D. Bloebaum, Salt Lake City, UT (US)

(73) Assignee: Aaron. A. Hofmann, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/509,282
(22) PCT Filed: Jul. 27, 1998
(86) PCT No.: PCT/US98/15500
§ 371 Date: Mar. 22, 2000
§ 102(e) Date: Mar. 22, 2000
(87) PCT Pub. No.: WO00/06055
PCT Pub. Date: Feb. 10, 2000

(51) Int. Cl.$^7$ .................................................. A61F 2/28
(52) U.S. Cl. ................................ 623/16.11; 623/18.11; 606/92
(58) Field of Search ........................ 623/16.11, 18.11, 623/20.14, 20.32, 20.15, 23.19, 23.2, 22, 39; 606/79, 92, 88; A61F 2/38

(56) References Cited

U.S. PATENT DOCUMENTS

| 3,774,244 A | 11/1973 | Walker |
| 3,816,855 A | 6/1974 | Saleh |
| 3,837,009 A | 9/1974 | Walker |
| 3,869,731 A | 3/1975 | Waugh et al. |
| 4,285,071 A | 8/1981 | Nelson et al. |
| 4,301,552 A | 11/1981 | London |
| 4,550,448 A | 11/1985 | Kenna |
| 4,563,778 A | 1/1986 | Roche et al. |
| 4,714,473 A | * 12/1987 | Bloebaum ................. 623/20.21 |
| 4,769,040 A | 9/1988 | Wevers |
| 4,883,488 A | * 11/1989 | Bloebaum et al. ........ 623/20.34 |
| 4,950,298 A | * 8/1990 | Gustilo et al. ............ 623/20.15 |
| 5,163,963 A | 11/1992 | Hewka et al. |
| 5,171,276 A | 12/1992 | Caspari et al. |
| 5,201,768 A | 4/1993 | Caspari et al. |

(List continued on next page.)

FOREIGN PATENT DOCUMENTS

| EP | 327297 | 8/1989 |
| EP | 531250 | 3/1993 |

OTHER PUBLICATIONS

A Cement Impactor for Uniform Cement Penetration in the Upper Tibia—Young–Hoo Kim, M.D., et al.
Jan.–Feb. 1984—Clinical Orthopedics & Related Research
Control of Cement Penetration in Total Knee Arthroplasty P.S. Walker, Ph.D., et al.
May 1984—Clinical Orthopedics and Related Research.

*Primary Examiner*—Bruce Snow
*Assistant Examiner*—Brian Pellegrino
(74) *Attorney, Agent, or Firm*—Kelly Bauersfeld Lowry & Kelley, LLP (57) ABSTRACT

A prosthetic joint and related placement method are provided for cemented fixation to a prepared patient bone, with a cement layer and mantle of controlled, predetermined thickness. The prosthetic component such as a tibial or femoral component for a knee prosthesis includes an attachment surface bounded by a flow restrictor wall which cooperates with the attachment surface to define an open-sided cavity for receiving a quantity of bone cement. An intruder tool is provided to form a shallow recess in the prepared patient bone for mating seated reception of the flow restrictor wall on the prosthetic component. In one form, the prosthetic component and the intruder tool may be adjustable to fit patient bones of different size.

28 Claims, 11 Drawing Sheets

U.S. PATENT DOCUMENTS

| | | |
|---|---|---|
| 5,217,498 A | 6/1993 | Henssge et al. |
| 5,246,459 A | 9/1993 | Elias |
| 5,263,987 A * | 11/1993 | Shah ...................... 623/18.11 |
| 5,290,311 A | 3/1994 | Baumann |
| 5,336,266 A | 8/1994 | Caspari et al. |
| 5,370,693 A | 12/1994 | Kelman et al. |
| 5,376,124 A | 12/1994 | Gustke et al. |
| 5,480,445 A | 1/1996 | Burkinshaw |
| 5,876,460 A | 3/1999 | Bloebaum |

\* cited by examiner

CEMENTED PROSTHETIC COMPONENT AND PLACEMENT METHOD

BACKGROUND OF THE INVENTION

This invention relates generally to improvements in prosthetic devices used for reconstructing human joints, such as a knee joint, hip joint, etc. More particularly, this invention relates to an improved prosthetic component and related method for cemented attachment of the prosthetic component to a prepared patient bone, in a manner achieving a substantially optimum strength attachment interface.

Artificial or prosthetic joint mechanisms for implantation into animals, particularly humans, have been the subject of intensive research and development efforts for many years. Such prosthetic joint mechanisms have typically comprised one or more implant components formed from a relatively biostable material having selected structural properties and a unique shape to replace all or part of a selected anatomical joint, for example, a hip or knee joint. The implant components are installed by surgically accessing the joint and by resection of one or more bone surfaces to accommodate direct attachment thereto of the implant components. One common attachment method has utilized bone cement, such as a methyl methacrylate-based cement or the like used as grouting material to fill up the space between the resected bone surface and the prosthetic component. Alternative attachment methods have relied upon surface coatings of controlled porosity on the prosthetic component in a position to achieve post-operative bone and/or tissue ingrowth.

Although cemented attachment of the prosthetic component can be performed relatively quickly and easily, and does not require a post-operative period during which the strength of the attachment interface is increased (e.g., by bone ingrowth), certain problems and disadvantages exist with respect to cemented components. More specifically, in a typical procedure, bone cement is applied to an attachment surface formed on the prosthetic component, and this attachment surface is then pressed against the prepared patient bone to achieve cemented fixation. However, during such press-on placement, some of the bone cement is normally extruded laterally outwardly from the attachment interface and is lost. Moreover, the prosthetic component can be pressed onto the patient's bone in a slightly cocked or tilted position, so that the thickness of the cement mantle is thicker in some areas and thinner in others. Such nonuniform cement mantle thickness can result in an attachment interface having less than optimum strength, thereby creating an undesired risk of post-operative separation of the prosthetic component from the patient bone.

There exists, therefore, a need for further improvements in prosthetic components of the type adapted for cemented attachment to a prepared patient bone, to provide a cement layer and mantle of controlled and substantially uniform thickness at the attachment interface. The present invention fulfills these needs and provides further related advantages.

SUMMARY OF THE INVENTION

In accordance with the invention, an improved prosthetic component and related placement method are provided for cemented attachment of the prosthetic component to a prepared patient bone, with a cement layer and mantle of controlled and substantially uniform thickness at the attachment interface. The prosthetic component of the present invention is adapted for use in various prosthetic joints, such as a knee joint or hip joint and the like.

The prosthetic component of the present invention includes an attachment surface of selected and typically grooved configuration with a size and shape for substantially mated fit with a resected patient bone. A plurality of spacer pegs having a selected height are desirably provided in the preferred form and protrude outwardly from the attachment surface. The attachment surface is bounded by a flow restrictor wall, which, when the spacer pegs are provided, has a selected height greater than the heights of the spacer pegs. In one preferred form, the flow restrictor defines an undercut inboard surface extending upwardly from the attachment surface.

An intruder tool is provided for engaging the resected patient bone to form a shallow recess having a size and shape for seated reception of the flow restrictor wall on the prosthetic component. In a preferred form, the intruder tool comprises a base plate with a projecting cutter rim thereon to engage the patient bone and form the shallow recess therein. The base plate and rim of the intruder tool define an open sided cavity which can be used for receiving a quantity of bone cement that can be pressed into porous cancellous bone during the step of forming the shallow recess.

The flow restrictor wall cooperates with the attachment surface of the prosthetic component to define an open-sided cavity for receiving an additional quantity of the bone cement. A leveler tool has a head shaped for mating press-in reception into the prosthetic component cavity to spread the bone cement in a uniform layer to a height at least slightly above the tops of the spacer pegs but below the rim of the flow restrictor wall, with excess bone cement escaping through vent ports formed in the leveler tool head.

The prosthetic component is then press-fitted onto the prepared patient bone, with the flow restrictor wall seated into the shallow recess. In this regard, the shallow recess is formed at an appropriate depth so that the flow restrictor wall when contacting the bottom of said recess functions to orient the attachment surface at a predetermined spacing from the prepared patient bone. This spacing is further regulated by inclusion of the spacer pegs which have a height to contact and seat upon the prepared patient bone when the flow restrictor wall is seated within the shallow recess. The bone cement contained within the prosthetic component cavity is thus confined by the restrictor wall against escape, for intrusion into the patient bone and further to form a substantially uniform thickness mantle in intimate surface-to-surface contact between the patient bone and the implant prosthesis. A strong, substantially optimum strength cemented attachment interface is thus achieved.

In accordance with an alternative preferred form of the invention, the prosthetic component and the intruder tool may be constructed for size adjustment to accommodate use with a range of patient bone sizes. In this form, the prosthetic component comprises a pair of component members respectively including a slidably interfitting key and keyway together with means for locking said component members with the key in a selected position of adjustment relative to the keyway. The two component members further include respective, generally U-shaped segments of the flow restrictor wall, with the ends of said U-shaped segments slidably overlapping within a range of size adjustment. The intruder tool also comprises a pair of tool members respectively including a slidably interfitting key and keyway with associated locking means, in combination with generally U-shaped cutter segments adapted to slidably overlap within a range of size adjustment to form the cutter rim.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
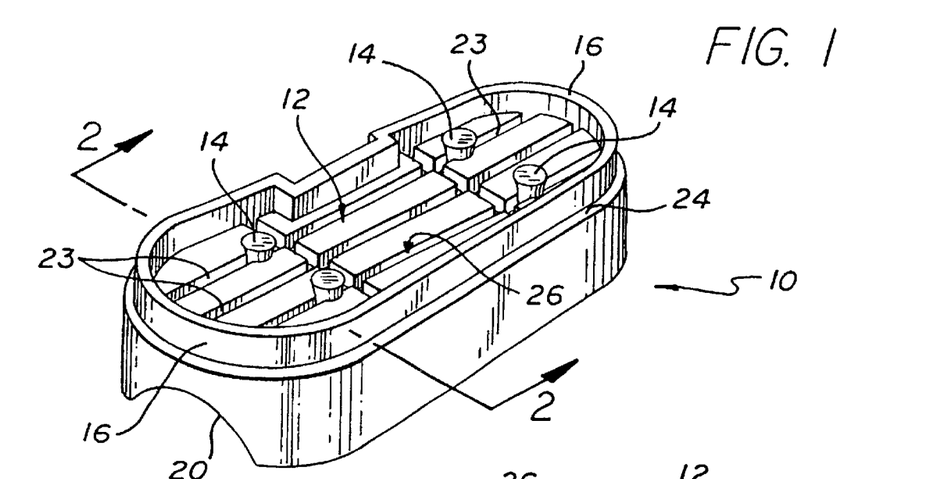
FIG. 1 is a perspective view illustrating one preferred form of an inverted tibial component for a knee prosthesis, constructed in accordance with the novel features of the invention.
Figure 2:
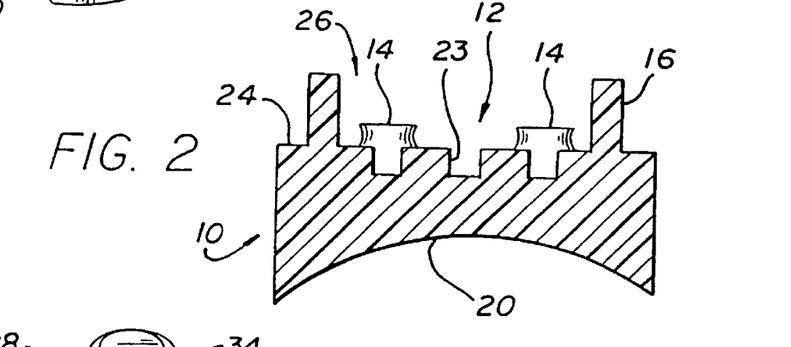
FIG. 2 is an anterior-posterior vertical sectional view taken generally on the line 2—2 of FIG. 1.
Figure 3:
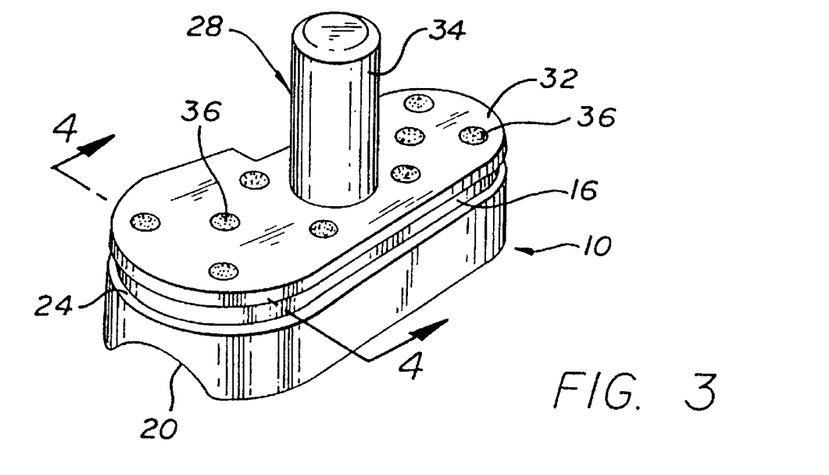
FIG. 3 is a perspective view showing a leveler tool for use in partial filling of an open-sided bone cement cavity defined by the prosthetic component.

As shown in the exemplary drawings, a prosthetic component referred to generally in FIG. 1 by the reference numeral 10 is provided for implantation into the body of a patient, in the course of reconstructing a joint such as a knee joint or hip joint. FIGS. 1–3 show the prosthetic component 10 in the form of a tibial component forming a portion of a knee prosthesis. As shown, the prosthetic component 10 includes an attachment surface 12 for cemented affixation to a prepared patient bone (FIGS. 5–8). The attachment surface 12 is depicted in the illustrative embodiment in association with a plurality of relatively short protruding spacer pegs 14 in combination with a surrounding taller flow restrictor wall 16, to achieve an attachment interface defined by a cement layer or mantle 18 (FIG. 8) of controlled and preferably substantially uniform thickness.

Figure 9:
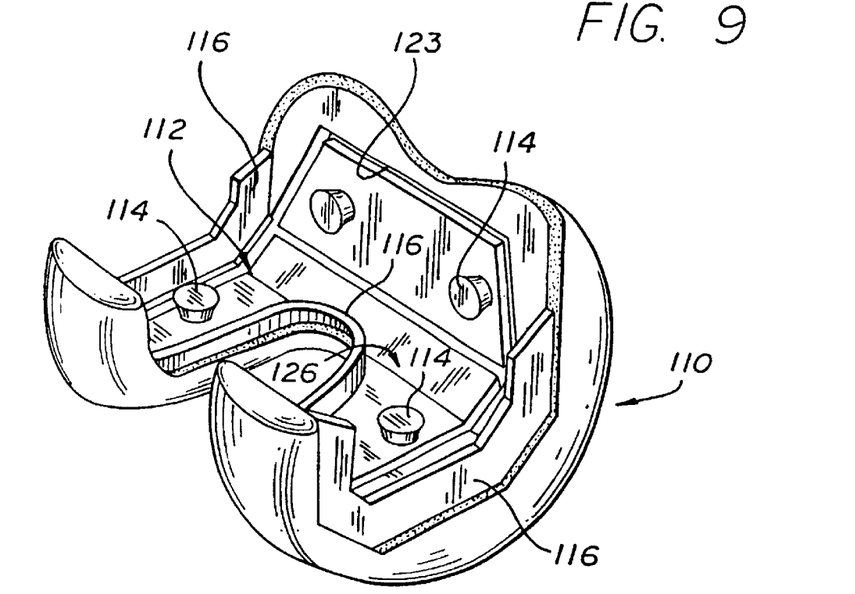
FIG. 9 is a perspective view illustrating a femoral component constructed in accordance with the invention.
Figure 10:
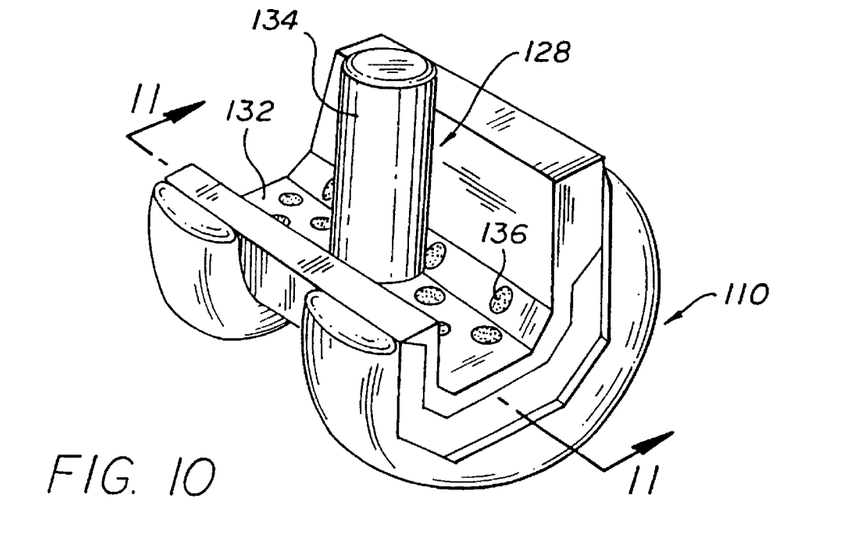
FIG. 10 is a perspective view showing a leveler tool for use in partial filling of an open-sided bone cement cavity defined by the femoral component of FIG. 9.
Figure 11:
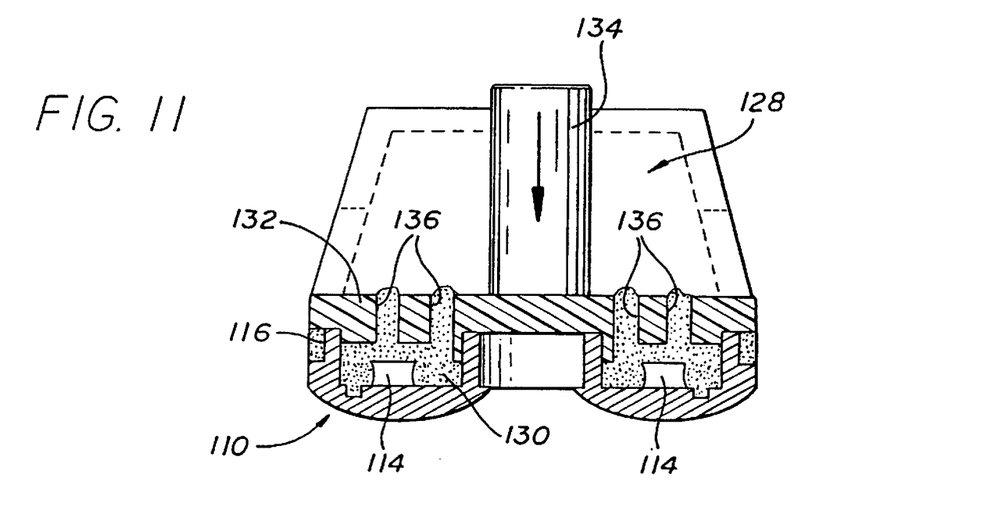
FIG. 11 is a vertical sectional view taken generally on the line 11—11 of FIG. 10.

The tibial prosthetic component 10 is shown in FIGS. 1–3 in an inverted orientation to illustrate construction details of the attachment surface 12 formed on the underside thereof, for subsequent affixation to the upper end of a prepared or resected patient tibia. The illustrative tibial component 10 traditionally provides an upwardly presented bearing member 20 shaped concavely to receive and support the convexly curved condyles of a mated femoral component (shown in FIG. 9). This bearing member 20 is commonly formed from a high density plastic material, such as polyethylene or the like. FIGS. 1–3 show the tibial component 10 having a unitary construction formed from high density plastic material, although it will be understood that the bearing member 20 can be provided as a separate component for assembly with a tibial tray or platform constructed from an alternate material such as titanium or titanium alloy or other suitable biocompatible material, or alternately as a tibial component formed entirely from a suitable biocompatible metal material.

The underside of the tibial component 10 defines the attachment surface 12 which commonly includes an array of shallow, intersecting grooves 23 formed in an otherwise substantially flat or planar surface. The spacer pegs 14 protrude outwardly from this flat surface with a controlled and preferably uniform height. As shown best in FIG. 1, in accordance with one preferred form of the invention, a medial pair and a lateral pair of the spacer pegs 14 are provided, each with a selected anterior-posterior spacing. In addition, the spacer pegs 14 have a curved, preferably concave profile shape for enhanced mechanical interlock with bone cement, as will be described in more detail.

The flow restrictor wall 16 surrounds or circumscribes the attachment surface 12 and the spacer pegs 14 protruding therefrom. In the preferred configuration, the flow restrictor wall 16 is inset a short distance from the periphery of the tibial component 10, to define a peripheral land 24 which may be constructed with a roughened surface texture or otherwise formed with a porous bone ingrowth surface. The height of the flow restrictor wall 16 is greater than the height of the spacer pegs 14, as shown best in FIGS. 1 and 2. In one preferred form, the spacer pegs 14 project upwardly from the attachment surface plane by a distance of about two millimeters, whereas the flow restrictor wall 16 projects upwardly from the attachment surface plane by a distance of about six millimeters. The flow restrictor wall 16 cooperates with the spacer pegs 14 and attachment surface 12 to define an open-sided cavity 26 for receiving a quantity of bone cement.

Figure 4:
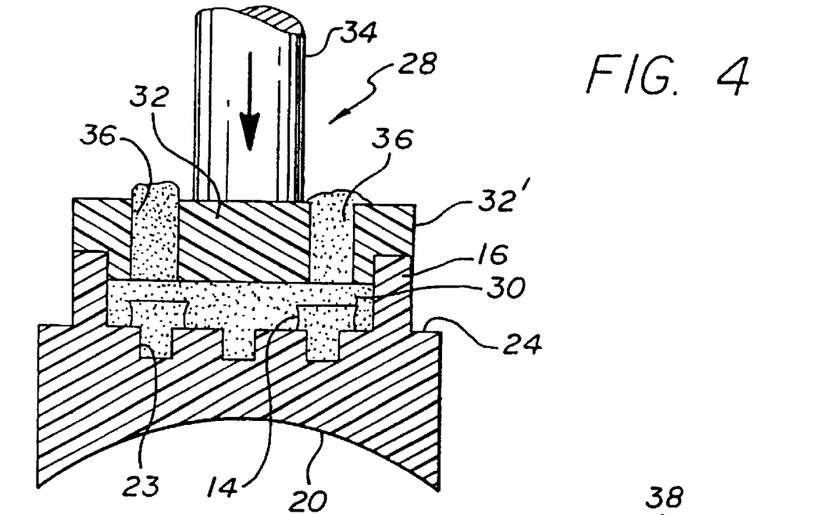
FIG. 4 is an anterior-posterior vertical sectional view taken generally on the line 4—4 of FIG. 3.

FIGS. 3 and 4 show a leveler tool 28 for use in partial filling of the bone cement cavity 26 of the tibial component 10 with a quantity of bone cement 30, to a substantially uniform depth. As shown, the leveler tool 28 has a head 32 mounted on a handle 34, wherein the head 32 has a size and shape for slide-fit press-in reception into the bone cement cavity 26 of the tibial component 10. An excess quantity of the bone cement 30 is initially placed into this cavity 26, and the leveler tool 28 is then used to distribute the bone cement 30 to a uniform depth. This distribution step occurs by pressing the tool head 32 into the cavity 26, to spread the bone cement to a uniform depth which is sufficient to cover the spacer pegs 14 but to be below the top of the flow restrictor wall 16. In a preferred configuration, the cement 30 is leveled within the cavity 26 to a depth approximately 2–4 mm above the tops of the pegs 14. FIG. 4 shows the head 32 of the leveler tool 28 pressed partially into the tibial component cavity 26, it being understood that the head 32 is pressed into the cavity 26 until an outer rim 32' engages the top of the flow restrictor well 16. Excess bone cement and air is allowed to escape through a plurality of vent ports 36 formed in the tool head 32.

Figure 5:
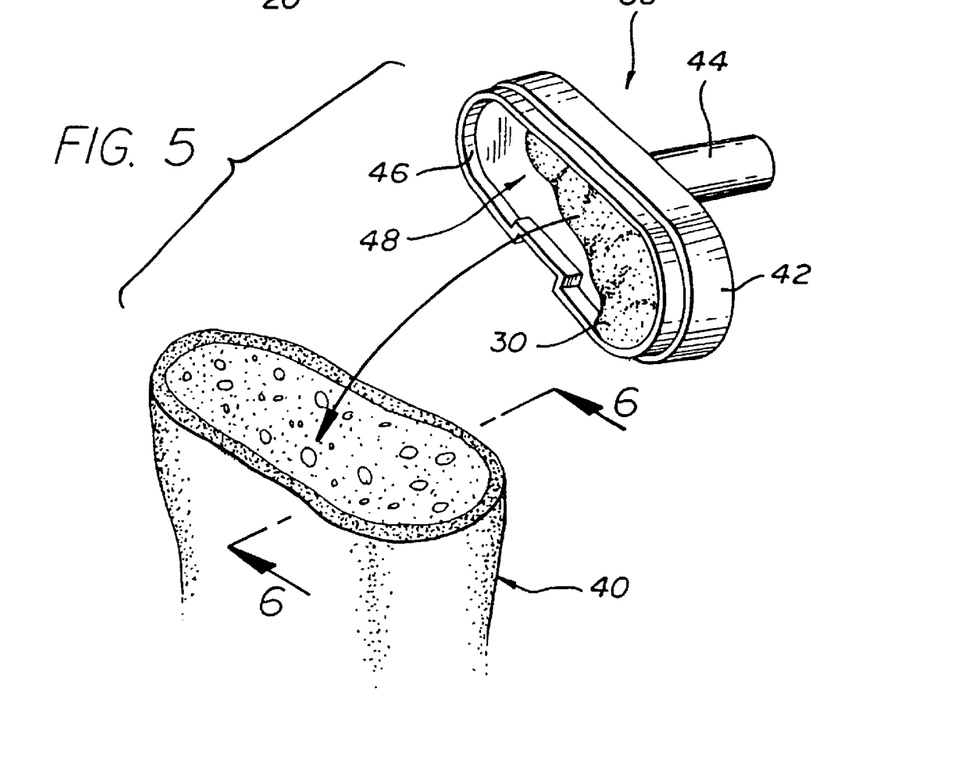
FIG. 5 is an exploded perspective view showing an intruder tool for use in shaping the upper end of a patient tibial bone.
Figures 6, 8:
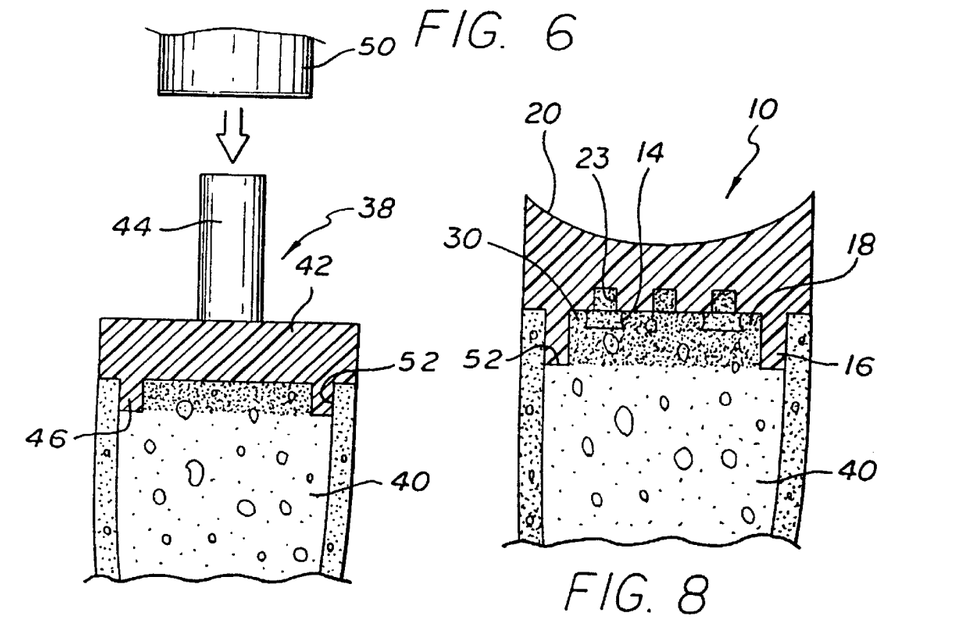
FIG. 6 is a fragmented vertical sectional view, taken generally on the line 6—6 of FIG. 5, and illustrating use of the intruder tool.
FIG. 8 is a fragmented vertical sectional view showing seated placement of the tibial component.

FIGS. 5 and 6 show an intruder tool 38 for use in shaping the upper end of the tibial bone 40 for subsequent cemented placement of the tibial component 10. As shown, the intruder tool 38 has a base plate 42 mounted on a handle 44, with an outwardly projecting cutter rim 46 formed with a configuration conforming to the flow restrictor wall 16 on the prosthetic component 10. The cutter rim 46 has a height, in the preferred form of the invention, corresponding to the difference between the height of the flow restrictor wall 16 and the spacer pegs 14. The cutter rim 46 cooperates with the base plate 42 to define a shallow cavity 48 which may optionally be used for receiving a quantity of the bone cement 30, with FIG. 5 depicting this cavity 48 in a partially filled state so as to illustrate construction details of the base plate 42 and cutter rim 46.

As shown in FIG. 6, the intruder tool 38 is pressed against the partially prepared patient bone 40. An impact tool 50 may be used to drive the intruder tool 38 against the patient bone, so that the cutter rim 46 forms a shallow recess 52 in the prepared patient bone. At the same time, the bone cement 30 carried by the intruder tool 38 is pressed into and fills the porous cancellous bone in the region bounded by the cutter rim 46.

Figure 7:
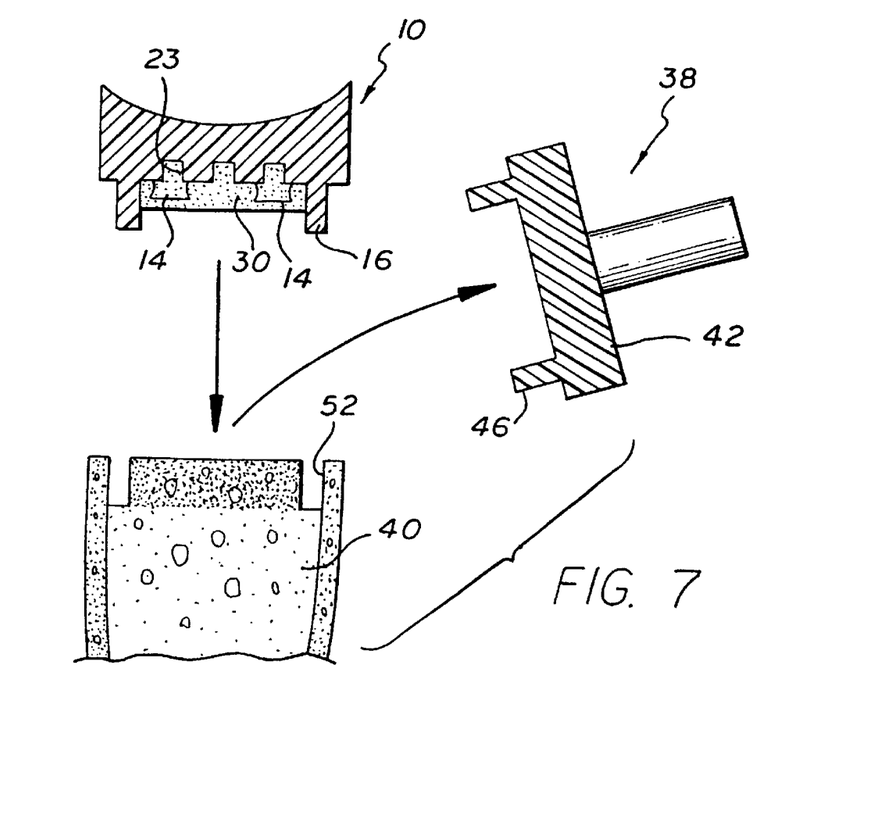
FIG. 7 is an exploded perspective view illustrating removal of the intruder tool and placement of the prosthetic component, relative to the prepared tibial bone.

As shown in FIGS. 7 and 8, the intruder tool 38 is then separated from the patient's bone 40, followed by press-on placement of the prosthetic component 10. The prosthetic component 10 is positioned with the flow restrictor wall 16 seated securely into the shallow recess 52. This positions the attachment surface 12 in a predetermined spaced relation with the prepared patient bone, with the plurality of spacer pegs 14 all firmly contacting the prepared patient bone. In this position, as shown best in FIG. 8, the bone cement 30 is pressed into the porous patient bone to form an interface layer in intimate knitted contact with the bone, and intimately joined to any bone cement previously pressed into the bone by the intruder tool 38. This bone cement 30 is also intimately contacted by the additional bone cement carried by the tibial component 10 in the region surrounding the spacer pegs 14, to define the minimum thickness cement mantle 18. This mantle 18 has a controlled and substantially uniform depth throughout the entire attachment interface. Importantly, the flow restrictor wall 16 cooperates with the mating recess 52 to confine the bone cement 30 against lateral escape, all resulting in a substantially optimized strength attachment.

FIGS. 9–15 show the invention with respect to an alternative prosthetic component, namely, a femoral component 110 for a prosthetic knee joint. The general construction of the femoral component 110 and the related attachment method conform to that previously shown and described with respect to the tibial component 10 depicted in FIGS. 1–8, whereby structures shown in FIGS. 9–15 which are directly analogous to those previously shown and described in FIGS. 1–8 will be identified by common reference numerals increased by 100.

More specifically, the femoral component 110 has a multifaceted geometry for substantially mated fit with a prepared lower end of a patient's femur 140 (FIGS. 12–15). The multifaceted configuration includes an attachment surface 112 with a plurality of upstanding short spacer pegs 114, in combination with a flow restrictor wall 116. Appropriate shallow grooves 123 are normally formed in the attachment surface 112. The spacer pegs 14 have a height which is less than the height of the flow restrictor wall 116. The flow restrictor wall 116 cooperates with the spacer pegs 114 and the attachment surface 112, to define an open-sided cavity 126 for receiving a quantity of bone cement 130 (FIG. 11) that is leveled to a depth above the tops of the spacer pegs 114 by means of a leveler tool 128 (FIGS. 10 and 11) similar to that previously described with respect to the tibial component 10. The leveler tool 128 includes a head 132 having vent ports 136 therein, and a handle 134.

Figure 12:
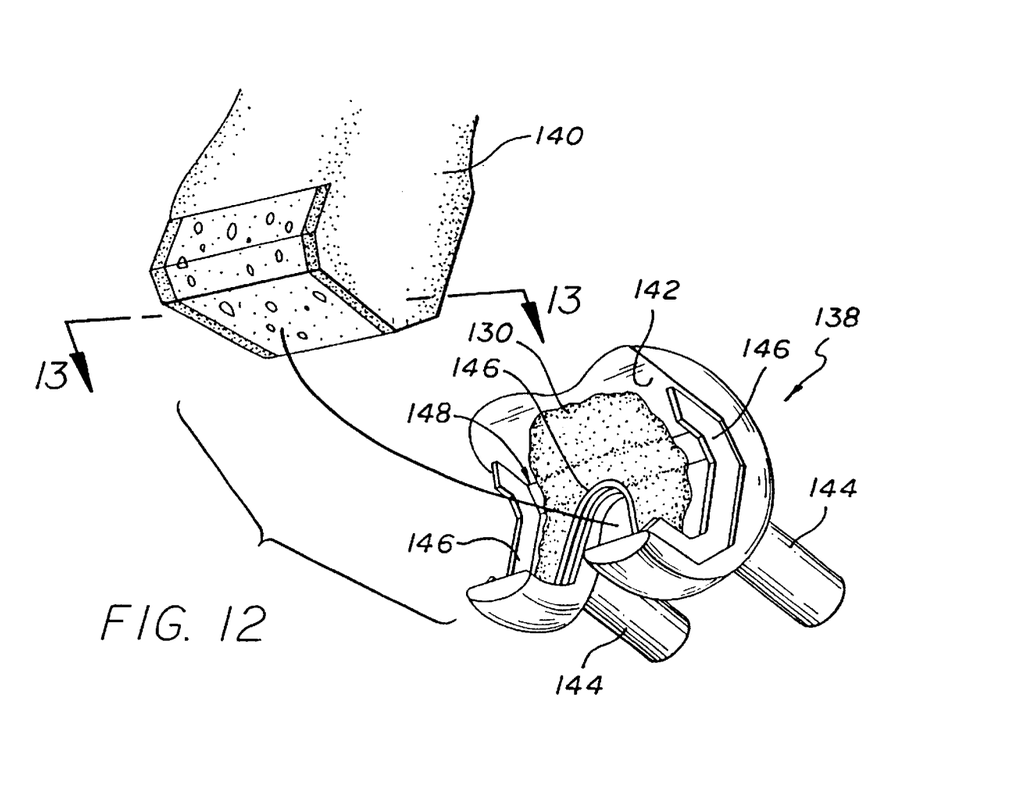
FIG. 12 is an exploded perspective view showing an intruder tool for use in shaping the lower end of a patient femoral bone.
Figure 13:
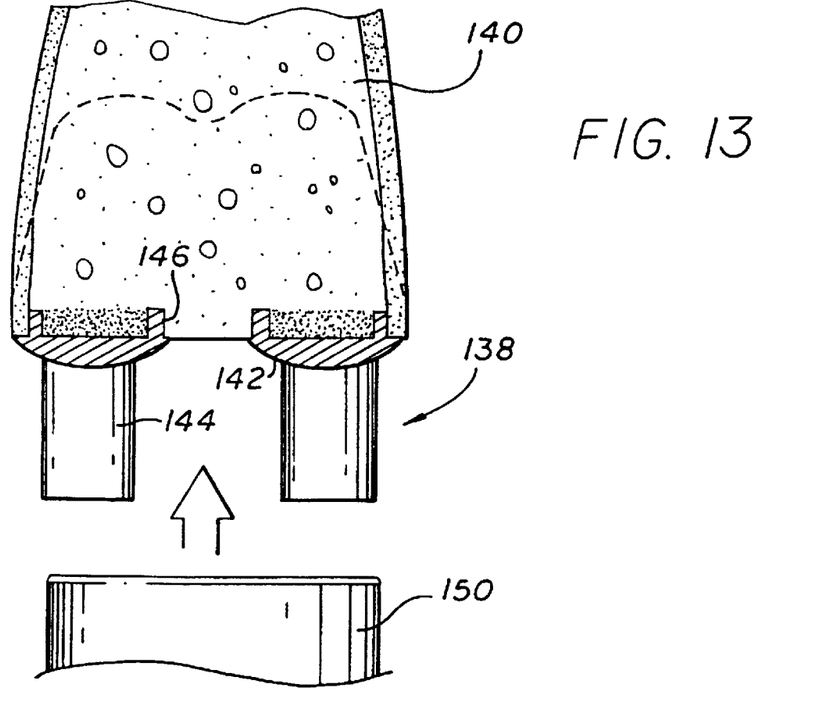
FIG. 13 is a fragmented vertical sectional view taken generally on the line 13—13 of FIG. 12, and illustrating use of the intruder tool.

An intruder tool 138 is provided as shown in FIGS. 12 and 13 for final shaping of the resected femoral bone 140 of the patient. As shown, the intruder tool 138 has a multifaceted base plate 142 mounted on a pair of handles 144, with a short cutter rim 146 protruding from the base plate in a configuration generally conforming to the flow restrictor wall 116 of the femoral component 110. An open-sided cavity 148 is thus defined on the intruder tool 138 which can be used for receiving a quantity of bone cement 130. Once again, the illustrative drawings show the cavity 148 only partially filled with bone cement 130, in order to reveal construction details of the intruder tool. The intruder tool is pressed and may be impacted with a tool 150 (FIG. 13) against the patient bone to form a shallow recess 152, and concurrently to drive the bone cement 130 into the porous cancellous bone.

Figure 14:
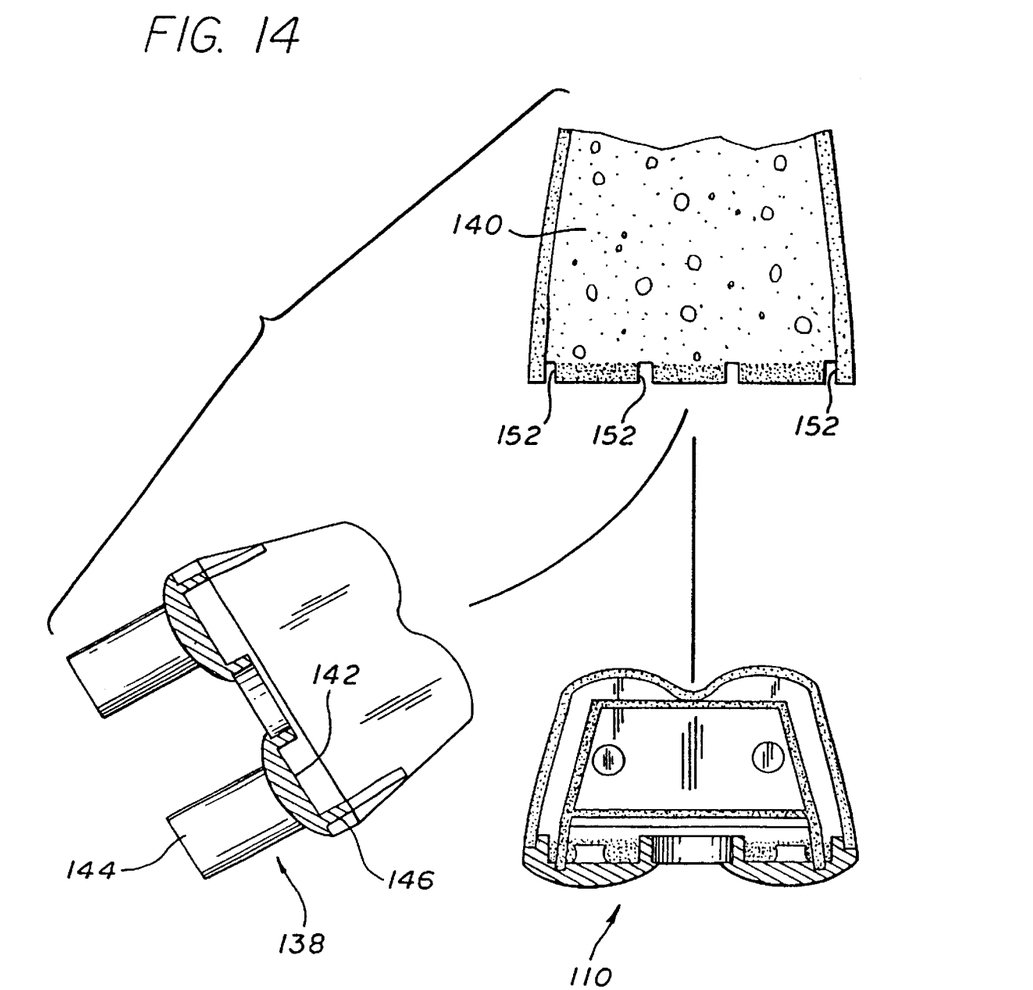
FIG. 14 is an exploded perspective view showing separation of the intruder tool from the femoral bone and placement of the femoral component thereon.
Figure 15:
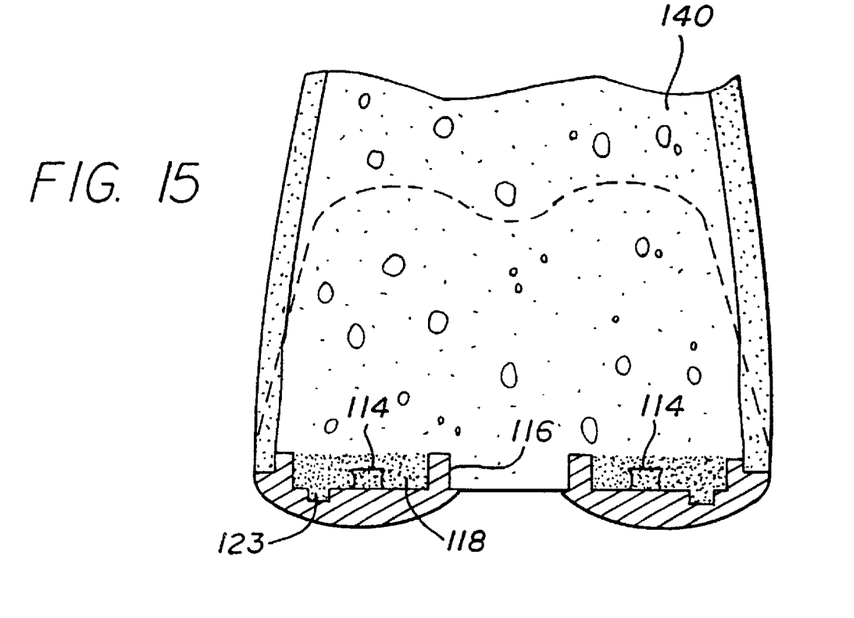
FIG. 15 is a fragmented vertical sectional view showing the femoral component mounted on the prepared patient bone.

Subsequent removal of the intruder tool (FIG. 14) permits seated placement of the femoral component 110 with bone cement previously placed therein, as viewed in FIGS. 14 and 15. The flow restrictor wall 116 is seated within the formed recess 152, with the spacer pegs 114 contacting the patient bone. As a result, a cement mantle 118 of controlled and preferably uniform thickness is provided across the attachment interface, and in intimate association with any bone cement previously pressed into the cancellous bone. A substantially optimum strength attachment interface results.

FIGS. 16–24 illustrate an alternative preferred form of the invention with respect to another tibial component 210 for a prosthetic knee joint, wherein the tibial component 210 and a related modified intruder tool 250 are adapted for size adjustment within a range of sizes to accommodate use with bones within a range of sizes in different patients. The overall construction and related attachment method again conform to that previously shown and described with respect to FIGS. 1–8, whereby structures depicted in FIGS. 16–24 which are directly analogous to those previously shown and described are identified by common reference numerals increased by 200.

More particularly, the tibial component 210 comprises a pair of slidably interconnected prosthetic component members 60 and 62 which, when assembled as shown in FIGS. 16–19, define an underside with an attachment surface 212 surrounded or circumscribed by the flow restrictor wall 216. The attachment surface 212 is shown without surface detail, but it will be understood that this attachment surface 212 may and typically will comprise an array of surface discontinuities such as the shallow intersecting grooves 23 depicted in FIG. 1. Moreover, FIGS. 16–20 illustrate a plurality of short spacer pegs 214 extending upwardly from the attachment surface 212, although such spacer pegs 214 are optional and may be omitted. The upper side of the tibial component 210 is adapted for seated reception and support of a suitable bearing member 220, such as by snap-fit mounting thereon into a cavity 64 as shown best in FIGS. 17 and 19.

The two prosthetic component members 60 and 62 (FIGS. 16–20) cooperatively define the flow restrictor wall 216. In this regard, the two prosthetic component members 60 and 62 are shown in the form of slidably interfitting medial and lateral components, respectively including an upstanding wall segment 66 and 68 of generally U-shaped geometry. These two wall segments 66, 68 are arranged, when the prosthetic component members 60, 62 are assembled, with their open sides facing each other. Importantly, the wall segments 66, 68 are sized so that the ends thereof slidably overlap to define the circumferential flow restrictor wall 216.

Figures 16, 17, 18:
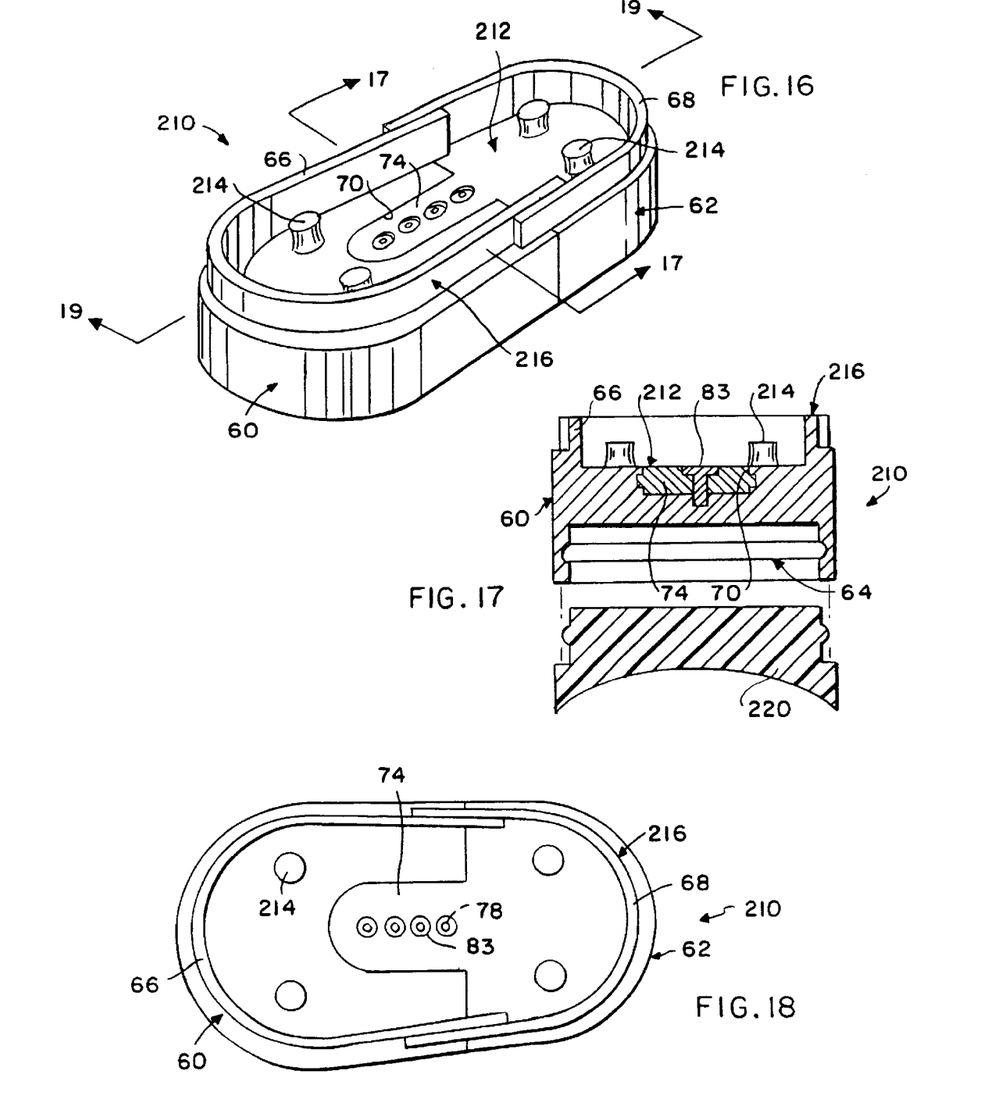
FIG. 16 is a perspective view illustrating an alternative form of an inverted tibial component for a knee prosthesis, constructed in accordance with the invention and adapted for size adjustment.
FIG. 17 is a anterior-posterior vertical sectional view taken generally on the line 17—17 of FIG. 16, and further depicting a bearing member in exploded relation with the tibial component.
FIG. 18 is a plan view of the tibial component of FIG. 16.
Figure 19:
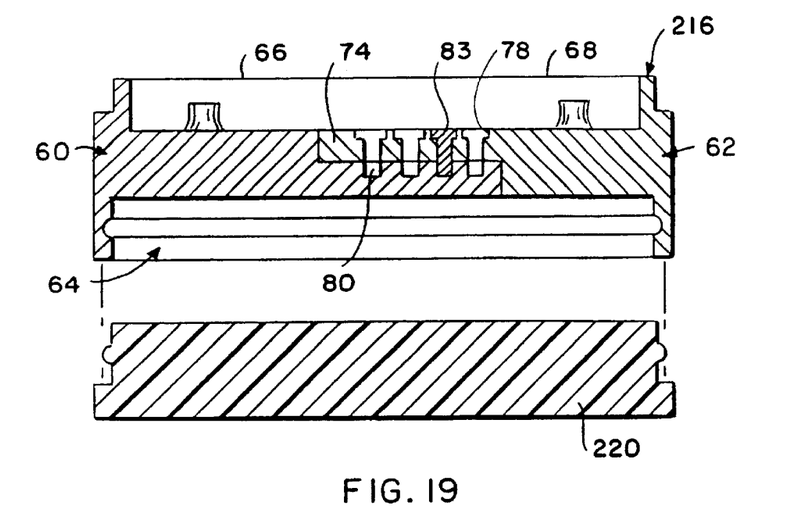
FIG. 19 is a medial-lateral vertical sectional view taken generally on the line 19—19 of FIG. 16, and depicting the bearing member in exploded relation with the tibial component.
Figure 20:
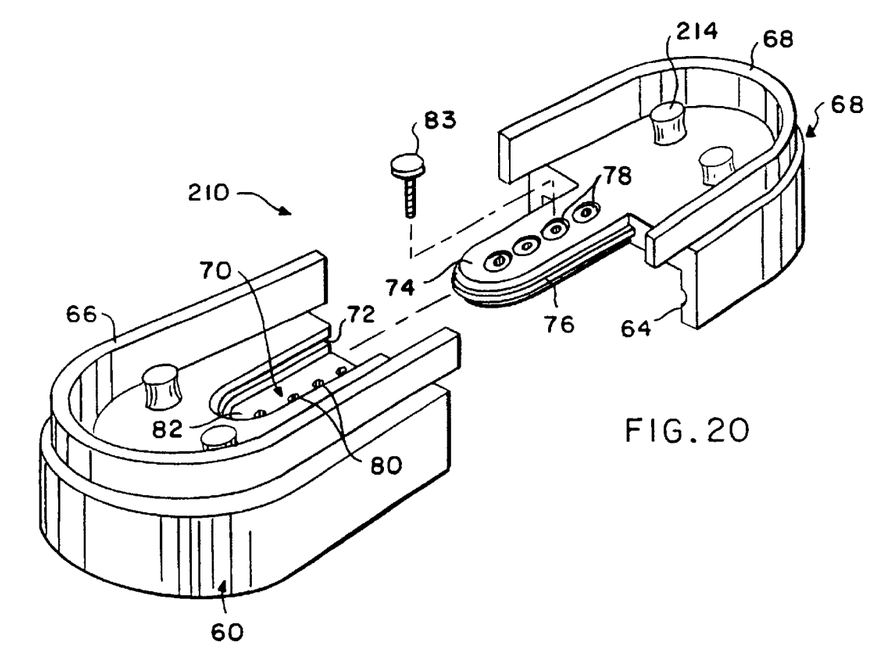
FIG. 20 is an exploded perspective view of the tibial component of FIG. 16.
Figure 21:
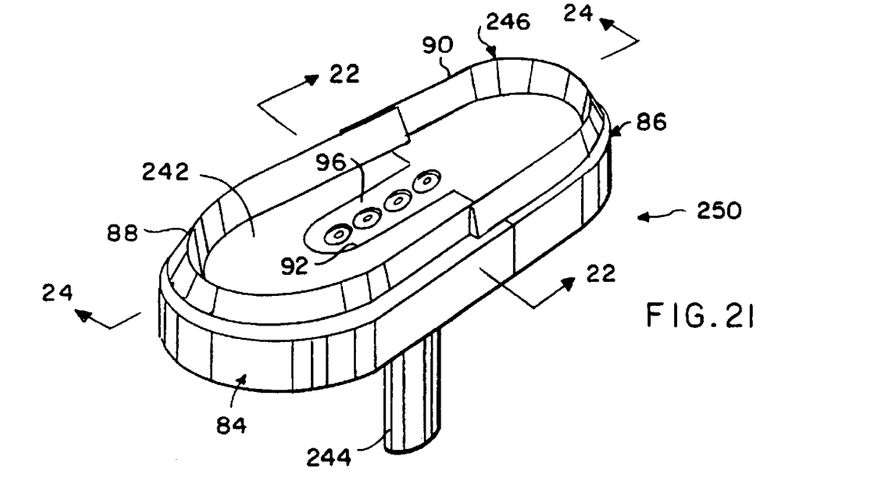
FIG. 21 is a perspective view of an intruder tool adapted for size adjustment, for use in conjunction with the tibial component of FIGS. 16–20.
Figure 22:
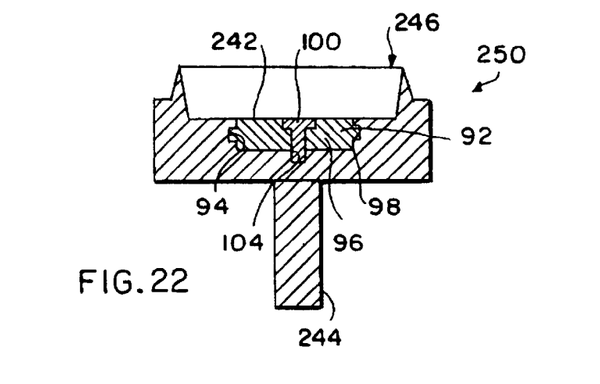
FIG. 22 is an anterior-posterior vertical sectional view taken generally on the line 22—22 of FIG. 21.
Figure 23:
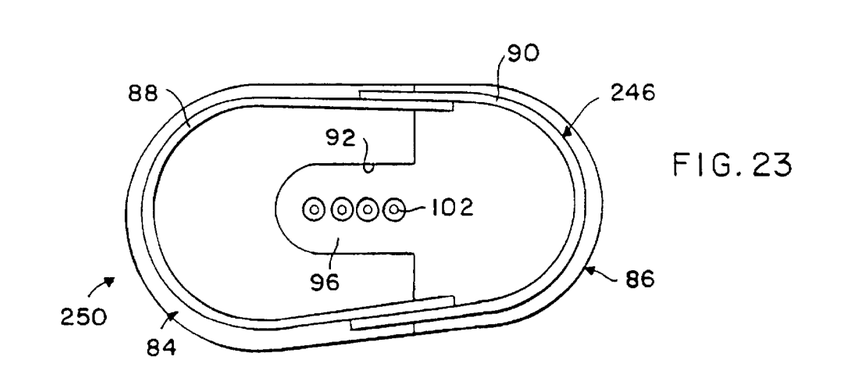
FIG. 23 is a plan view of the intruder tool of FIG. 21.
Figure 24:
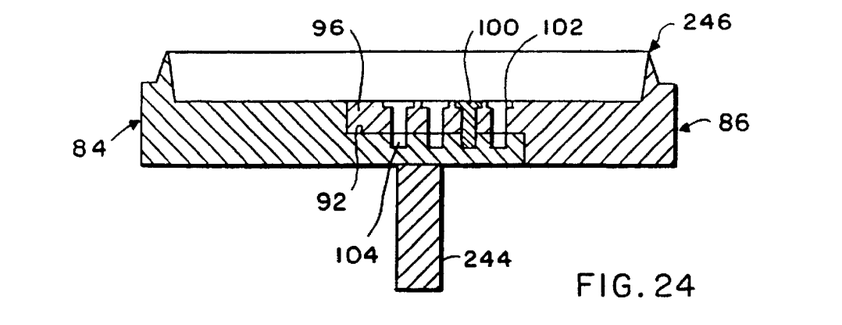
FIG. 24 is a medial-lateral vertical sectional view taken generally on the line 24—24 of FIG. 21.

The prosthetic component member 60 is configured to define a laterally open keyway 70 formed generally centrally within the attachment surface portion thereof, to open along a medial-lateral axis. As shown in FIGS. 17 and 20, this keyway 70 includes an undercut groove 72. The other prosthetic component member 62 is configured to define a laterally projecting key 74 protruding as an extension of the attachment surface thereof along a medial-lateral axis, for substantially mating slide-fit reception into the keyway 70. This key 74 defines a side edge with an outwardly extending lip 76 for slide-fit reception into the keyway groove 72. With this construction, the two prosthetic component members are slidably interfitted in a manner to accommodate adjustment in size in the medial-lateral direction, in order to adjust the tibial component 210 for appropriately fitting the prepared patient bone in a particular patient. Throughout a significant range of size adjustment, the wall segments 66, 68 slidably overlap to define the circumscribing flow restrictor wall 216.

Locking means are provided for securely interlocking the two prosthetic component members in the desired position of adjustment. FIGS. 16–20 shown the locking means in one preferred form, to include a plurality of downwardly open and desirably countersunk screw ports 78 formed at spaced locations along the length of the key 74. These screw ports 78 are aligned with underlying threaded bores 80 formed in a base 82 of the keyway 70. This arrangement provides multiple positions of medial-lateral adjustment to align one or more screw ports 78 with the bores 80, and then to permit secure component interlock by installing one or more lock screws 83.

FIGS. 21–24 show the modified intruder tool 250 for use in the method of installing the tibial component 210 of FIGS. 16–20. As shown, the modified intruder tool 250 comprises the base plate 242 defined cooperatively by a pair of tool members 84 and 86 designed for adjustable slide-fit interconnection. The two tool members 84 and 86 form the upstanding circumscribing cutter rim 246, by means of a respective pair of generally U-shaped rim segments 88 and 90 which have their open sides assembled in slidably overlapping and interfitting relation. Similar to the counterpart tibial component 210, the tool member 84 defines a central and laterally open keyway 92 lined by a groove 94 for slide-fit reception of a central and laterally extending key 96 having an edge with a protruding lip 98 on the tool member 86. One or more lock screws 100 are fastened through one or more screw ports 102 in the key 96 and into underlying threaded bores 104 in a surface below the keyway 92, for interlocking the tool member 84, 86 together in a selected size adjustment position. A handle 244 is provided on the tool member 84.

Figure 25:
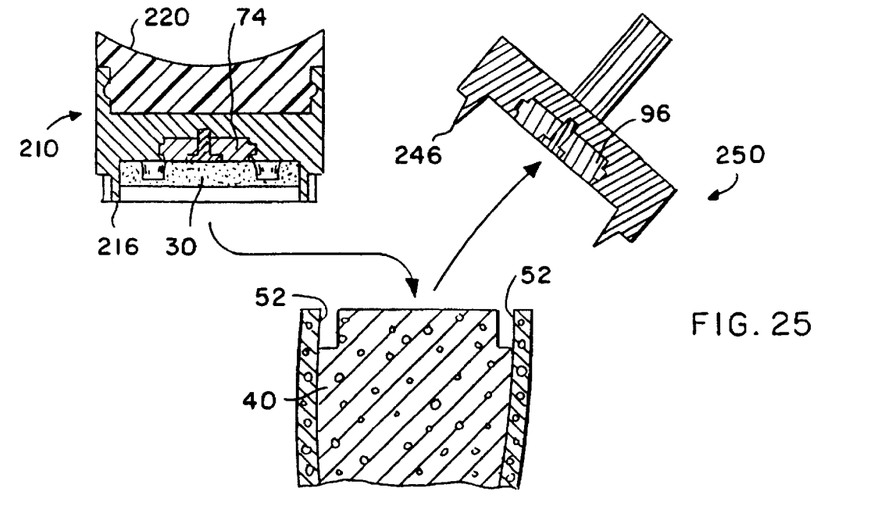
FIG. 25 is an exploded perspective view illustrating removal of the intruder tool of FIG. 21 and placement of the tibial component of FIG. 16, relative to the prepared patient bone.

In use, the tibial component 210 is size adjusted for appropriate fit with the prepared patient bone 40, as viewed in FIG. 25. The intruder tool 250 is then sized adjusted to the same size and the tibial component. The intruder tool 250 can then be utilized as previously described with respect to FIGS. 5–7 to cut a shallow recess 52 (FIG. 25) in the prepared patient bone 40. Thereafter, the tibial component 210 is appropriately loaded with bone cement 30 and then placed against the patient bone with the flow restrictor wall 216 seated within the shallow recess 52. The flow restrictor wall 216 bottoms out within the recess 52, to position the attachment surface 212 at the selected and substantially uniform spacing from the bone surface. The spacer pegs 214, if provided, additionally contact the patient bone to insure correct fit.

Figure 26:
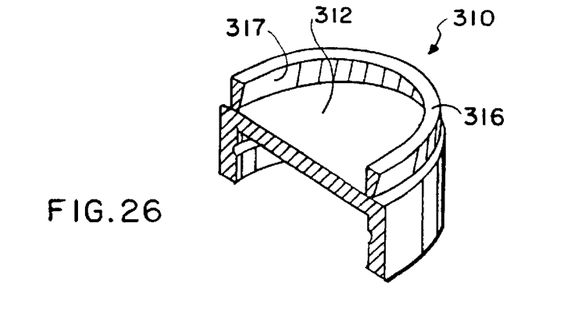
FIG. 26 is a perspective view, shown partially in vertical section, of a portion of a tibial component formed in accordance with a further alternative preferred form of the invention.

FIG. 26 illustrates a further modification to the invention, applicable to each of the above described embodiments. FIG. 26 shows a portion of a tibial component 310 which can be constructed according to the tibial component 10 of FIG. 1 or the tibial component 210 of FIG. 16. In this version, the tibial component 310 includes an attachment surface 312 surrounded or circumscribed by an upstanding flow restrictor wall 316. Importantly, the flow restrictor wall 316 defines an inboard face 317 extending upwardly from the attachment surface 312, wherein this inboard face 317 is undercut. In the preferred geometry, the inboard wall face 317 extends from the attachment surface 312 angularly upwardly and inwardly as viewed in FIG. 26, and then terminates in a short upwardly extending segment. The undercut face 317 effectively interlocks with bone cement when the tibial component is seated upon a prepared patient bone.

A wide variety of further modifications and improvements to the prosthetic component 10 and related attachment method of the present invention will be apparent to persons skilled in the art. In this regard, it will be understood and appreciated that the principles of the invention can be applied to a variety of prosthetic joint components, including patellar implants for knee joints, acetabular cups for hip joints, and other prosthetic devices. Accordingly, no limitation on the invention is intended by way of the foregoing description and accompanying drawings, except as set forth in the appended claims.

What is claimed is:

1. A prosthetic joint system for substantially mated fit of a prosthetic joint component with and cemented attachment to a prepared patient bone, said system comprising:

a prosthetic joint component defining an attachment surface, and a flow restrictor wall bounding at least a portion of said attachment surface, said attachment surface and said flow restrictor wall cooperatively defining an open-sided cavity for receiving a quantity of bone cement;

said flow restrictor wall having a size and shape for substantially mated fit with the prepared patient bone;

said flow restrictor wall defining means for preventing escape of any substantial portion of the bone cement within said cavity from between said attachment surface and the prepared patient bone when the prosthetic joint component is fitted with the prepared patient bone; and further including means for forming a shallow recess in the prepared patient bone, said recess having a size and shape for substantially mated fit reception of said flow restrictor wall when said prosthetic component is fitted with the prepared patient bone.

2. The system of claim 1 wherein said attachment surface has at least one groove formed therein.

3. The system of claim 1 further including at least one spacer peg protruding upwardly from said attachment surface with a height less than the height of said flow restrictor wall, said at least one spacer peg maintaining said attachment surface in predetermined spaced relation with the prepared patient bone when the prosthetic joint component is fitted therewith to form a bone cement mantle of predetermined thickness between said attachment surface and the prepared patient bone.

4. The system of claim 3 wherein said at least one spacer peg comprises a plurality of spacer pegs.

5. The system of claim 3 wherein said spacer peg has a nonlinear profile shape.

6. The system of claim 1 wherein said flow restrictor wall circumscribes said attachment surface.

7. The system of claim 1 wherein said prosthetic component comprises a pair of slidably interfitting component members for selectively adjusting the size of said prosthetic component, and including lock means for securing said interfitting component members in a selected position of size adjustment.

8. The system of claim 7 wherein said interfitting component members respectively include a pair of generally U-shaped wall segments having the open ends thereof in slidably overlapping and interfitting relation when said component members are slidably interfitted with each other, said wall segments cooperatively defining said flow restrictor wall.

9. The system of claim 7 wherein said pair of slidably interfitting component members respectively include a slidably interfitting key and keyway.

10. The system of claim 7 wherein said lock means comprises at least one lock screw interconnecting said pair of slidably interfitting component members in one of a plurality of size adjustment positions.

11. The system of claim 1 wherein said flow restrictor wall defines an undercut inboard face extending upwardly from said attachment surface.

12. The system of claim 1 wherein said recess forming means comprises an intruder tool having a base plate with a cutter rim protruding therefrom for engaging the prepared patient bone to form said recess.

13. The system of claim 12 wherein said intruder tool comprises a pair of slidably interfitting tool sections for selectively adjusting the size of said intruder tool, and including lock means for securing said interfitting tool sections in a selected position of size adjustment.

14. The system of claim 13 wherein said interfitting tool sections respectively include a pair of generally U-shaped cutter rim segments each with an open end, and having the open ends thereof in slidably overlapping and interfitting relation when said tool sections are slidably interfitted with each other, said cutter rim segments cooperatively defining said cutter rim.

15. The system of claim 13 wherein said pair of slidably interfitting tool sections respectively include a slidably interfitting key and keyway.

16. The system of claim 13 wherein said lock means comprises at least one lock screw interconnecting said pair of slidably interfitting tool sections.

17. The system of claim 1 wherein said recess forming means further includes means for pressing a quantity of bone cement into the prepared patient bone at a location adjacent to said attachment surface when said prosthetic component is fitted with the prepared patient bone.

18. The system of claim 3 further including means for filling said cavity in said prosthetic component with a quantity of bone cement in a layer having a depth at least slightly greater than the height of said spacer peg.

19. The system of claim 18 wherein said filling means comprises a leveler tool having a head for substantially mated sliding reception into said cavity, said head having a plurality of vent ports formed therein.

20. A method of cemented attachment of a prosthetic component to a prepared patient bone, said method comprising the steps of:

forming a prosthetic component with an attachment surface, and a flow restrictor wall bounding at least a portion of the attachment surface, whereby the flow restrictor wall and attachment surface cooperatively define an open-sided cavity;

at least partially filling the cavity in the prosthetic component with a quantity of bone cement;

shaping the prepared patient bone for substantially mated fit with the flow restrictor wall of the prosthetic component so that the flow restrictor wall substantially prevents escape of any substantial portion of the bone cement within the cavity when the prosthetic component is fitted with the prepared patient bone; and fitting the prosthetic component with the prepared patient bone with the flow restrictor wall matingly fitting the bone, to form a bone cement mantle of predetermined thickness between the attachment surface and the prepared patient bone.

21. The method of claim 20 wherein said step of forming the prosthetic component includes forming at least one spacer peg protruding outwardly from the attachment surface with a selected height less than the height of the flow restrictor wall, and further wherein said step of partially filling the cavity in the prosthetic component with a quantity of bone cement comprises filling the cavity with a layer of the bone cement at least slightly greater than the height of the spacer peg.

22. The method of claim 20 wherein said prosthetic component forming step comprises forming the attachment surface with at least one groove therein.

23. The method of claim 20 wherein said prosthetic component forming step comprises forming a plurality of spacer pegs to protrude outwardly from the attachment surface.

24. The method of claim 20 wherein said prosthetic component forming step comprises forming the flow restrictor wall to circumscribe the attachment surface.

25. The method of claim 20 wherein said shaping step comprises forming a shallow recess in the prepared patient bone for seated reception of the flow restrictor wall.

26. The method of claim 20 further including the step of pressing a quantity of bone cement into the prepared patient bone at a location adjacent to said attachment surface when said prosthetic component is fitted with the prepared patient bone.

27. The method of claim 20 wherein said prosthetic component forming step further includes forming the prosthetic component from a pair of slidably interfitting component members for adjustably sizing the prosthetic component.

28. The method of claim 20 wherein said prosthetic component forming step further comprises forming the flow restrictor wall with an undercut inboard face.

* * * * *